US012599605B2

(12) United States Patent
Chamorro Sánchez et al.

(10) Patent No.: US 12,599,605 B2
(45) Date of Patent: Apr. 14, 2026

(54) URIC ACID LIPOSOMES

(71) Applicants: HOSPITAL CLINIC DE BARCELONA, Barcelona (ES); FUNDACIÓ DE RECERCA CLÍNIC BARCELONA-INSTITUT D'INVESTIGACIONS BIOMÈDIQUES AUGUST PI I SUNYER, Barcelona (ES); AGENCIA ESTATAL CONSEJO SUPERIOR DE INVESTIGACIONES CIENTÍFICAS, M.P., Madrid (ES)

(72) Inventors: Angel Chamorro Sánchez, Sant Cugat del Vallès (ES); Ana María Planas Obradors, Barcelona (ES); Pedro Ramos Cabrer, San Sebastián (ES)

(73) Assignees: HOSPITAL CLINIC DE BARCELONA, Barcelona (ES); FUNDACIÓ DE RECERCA CLÍNIC BARCELONA-INSTITUT D'INVESTIGACIONS BIOMÈDIQUES AUGUST PII SUNYER, Barcelona (ES); AGENCIA ESTATAL CONSEJO SUPERIOR DE INVESTIGACIONES CIENTÍFICAS, M.P., Madrid (ES)

( * ) Notice: Subject to any disclaimer, the term of this patent is extended or adjusted under 35 U.S.C. 154(b) by 206 days.

(21) Appl. No.: 18/693,714

(22) PCT Filed: Oct. 25, 2022

(86) PCT No.: PCT/EP2022/079717
§ 371 (c)(1),
(2) Date: Mar. 20, 2024

(87) PCT Pub. No.: WO2023/072903
PCT Pub. Date: May 4, 2023

(65) Prior Publication Data
US 2024/0390381 A1      Nov. 28, 2024

(30) Foreign Application Priority Data

Oct. 29, 2021    (EP) ..................................... 21382979

(51) Int. Cl.
| | |
|---|---|
| *A61K 31/522* | (2006.01) |
| *A61K 9/1272* | (2025.01) |
| *A61K 9/1278* | (2025.01) |
| *A61P 9/10* | (2006.01) |

(52) U.S. Cl.
CPC .......... *A61K 31/522* (2013.01); *A61K 9/1272* (2013.01); *A61K 9/1278* (2013.01); *A61P 9/10* (2018.01)

(58) Field of Classification Search
CPC ..... A61K 31/522; A61K 9/1272; A61K 9/127
See application file for complete search history.

(56) References Cited

U.S. PATENT DOCUMENTS

| | | | |
|---|---|---|---|
| 2008/0193509 A1* | 8/2008 | Yoshino ............. | A61K 31/4745 514/283 |
| 2016/0256389 A1* | 9/2016 | Zhu ...................... | A61K 9/1271 |

FOREIGN PATENT DOCUMENTS

| | | |
|---|---|---|
| CN | 102230939 A | 11/2011 |
| WO | 2010112113 A1 | 10/2010 |
| WO | 2018206826 A1 | 11/2018 |

OTHER PUBLICATIONS

Zhong, Z. et al. "An electrochemical immunosensor for simultaneous multiplexed detection of neuron-specific enolase and pro-gastrin-releasing peptide using liposomes as enhancer" Electrochimica Acta 56 (2011) 5624-5629 (Year: 2011).*

Vanbever, R. et al. "Cationic Nanoliposomes Are Efficiently Taken up by Alveolar Macrophages but Have Little Access to Dendritic Cells and Interstitial Macrophages in the Normal and CpG-Stimulated Lungs" Mol. Pharmaceutics 2019, 16, 2048-2059 (Year: 2019).*

Zhong et al., "An electrochemical immunosensor for simultaneous multiplexed detection of neuron-specific enolase and pro-gastrin-releasing peptide using liposomes as enhancer", Electrochimica Acta, 2011, vol. 56, No. 16, pp. 5624-5629.

Mulder et al., "Lipid-based nanoparticles for contrast-enhanced MRI and molecular imaging", NMR in Biomedicine, 2006, vol. 19, pp. 142-164.

International Search Report and Written Opinion for Corresponding International Application No. PCT/EP2022/079717, 14 pages, Apr. 4, 2023.

International Preliminary Report on Patentability for Corresponding International Application No. PCT/EP2022/079717, 21 pages, Oct. 18, 2023.

* cited by examiner

*Primary Examiner* — Andrew S Rosenthal

(74) *Attorney, Agent, or Firm* — LUCAS & MERCANTI, LLP

(57) ABSTRACT

The present invention relates to liposomes that encapsulate uric acid, methods for its preparation and uses of said liposomes.

14 Claims, 4 Drawing Sheets

Co-location

Figure 1:
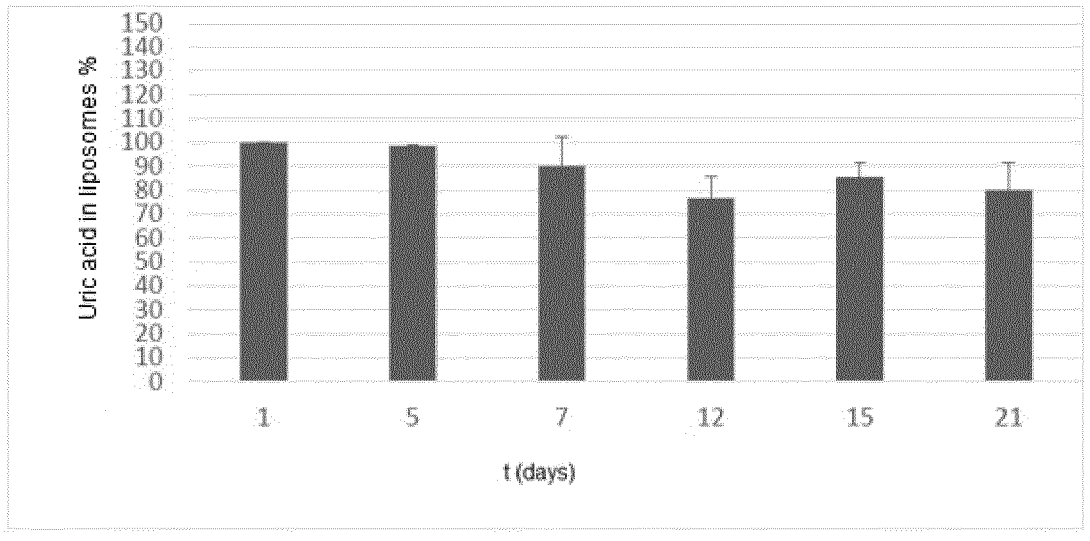

Liposomes: green
Blood vessels: red

Liposomes: green

Blood vessels: red

URIC ACID LIPOSOMES

CROSS-REFERENCE TO RELATED APPLICATION

This application is a 371 of PCT/EP2022/079717, filed Oct. 25, 2022, which claims the benefit of European Patent Application No. 21382979.9, filed Oct. 29, 2021, each of which are incorporated herein by reference

TECHNICAL FIELD

The present invention relates to the pharmaceutical and biomedical field, more specifically to new liposomes that encapsulate uric acid and their manufacturing process. Additionally, the present invention also relates to the treatment of cerebrovascular diseases, more preferably stroke.

BACKGROUND OF THE INVENTION

Cell death after stroke is the result of the complex interaction of excitotoxicity, acidosis, inflammation, oxidative stress, periinfarct depolarization, and apoptosis.

The term apoptosis is used synonymously with programmed cell death (hereinafter, MCP (by its acronym in Spanish)); however, apoptosis was originally defined as a set of morphological changes that occur after MCP. In developing neurons, these changes include chromatin condensation and cleavage and the formation of so-called apoptotic bodies. These changes are different from the morphological changes that characterize inflammation due to necrosis of the cytoplasmic organelles and the rupture of the mitochondrial and cytoplasmic membrane.

A mild ischemic injury usually induces cell death through an apoptotic-like mechanism rather than necrosis. Activators of apoptosis include oxygen free radicals, binding to death receptors, DNA damage, protease activation, and ion balance imbalance. Several experimental studies have shown that inhibition of apoptosis reduces the severity of ischemic injury.

Activation of caspases is a consequence of the activation of the intrinsic apoptosis pathway in which the mitochondria plays a fundamental role. Mitochondrial dysfunction and the opening of the mitochondrial transient permeability pore can result in caspase activation through the exit of Cytochrome C into the cytoplasm; however, there are other different mechanisms by which mitochondrial dysfunction can contribute to ischemic neuronal death. Severely damaged mitochondria may be unable to maintain the electrochemical gradient necessary for respiration and glucose oxidation. Thus, mitochondrial dysfunction can aggravate ischemic injury by exacerbating energy failure. Dysfunctional mitochondria also produce oxygen or nitrogen free radicals and non-radical substances that damage other cell organelles and DNA. Therefore, treatments that prevent mitochondrial dysfunction could be a more powerful neuroprotective strategy than caspase inhibition.

High $Ca^2$, $Na^+$ and ADP (adenosine diphosphate) intracellular levels cause the mitochondria to produce harmful levels of reactive oxygen or nitrogen species. Unlike other organs, the brain is especially vulnerable to reactive oxygen or nitrogen species because neurons have relatively low levels of endogenous antioxidants. The abundance of oxygen or nitrogen radicals causes the destruction of cellular macromolecules and participates in signaling mechanisms that cause apoptotic cell death. Ischemia activates nitric oxide synthase (hereinafter NOS) and increases the generation of nitric oxide (hereinafter NO), which combines with superoxide to produce peroxynitrite, a potent pro-oxidant agent. NO production and oxidative and nitrosative stress are also linked to the overactivation of poly (ADP-ribose) polymerase-1 (hereinafter, PARP-1), a DNA repair enzyme.

After reperfusion, there is an increase in the production of superoxide, NO and peroxynitrite. The formation of these radicals in the vicinity of blood vessels plays an important role in the injury induced by reperfusion and in the appearance of insufficient reperfusion despite adequate proximal recanalization (non-reflux phenomenon). These radicals activate metalloproteases (hereinafter, MMP), which degrade collagen and laminins in the basal lamina, disrupt the integrity of the vascular wall, and increase the permeability of the blood-brain barrier (hereinafter, BBB). Oxidative and nitrosilative stress also activate the recruitment and migration of neutrophils and other leukocytes into the cerebral vasculature, which release enzymes that further increase degradation of the basal lamina and vascular permeability. These events can lead to parenchymal hemorrhage, vasogenic cerebral edema, and leukocyte infiltration within the brain. Oxidative and nitrosative stress constricts the pericytes or muscle cells that surround the capillaries and prevents adequate perfusion of microcirculation despite the normalization of blood circulation in leptomeningeal vessels.

Uric acid is a powerful antioxidant agent that blocks reaction between superoxide anion and nitric oxide, which damages cells by nitrosylating tyrosine residues from proteins. Plasma concentration of uric acid is almost 10 times higher than that of other antioxidant substances, such as vitamins C or E, and its antioxidant capacity is higher. In addition, uric acid prevents degradation of extracellular superoxide dismutase, an essential enzyme for normal endothelial function. In hippocampal cell culture, uric acid protects against excitotoxic glutamate damage, stabilizing calcium homeostasis and preserving mitochondrial function. Also, uric acid has shown inhibition of the Fenton reaction. Beyond its antioxidant effects, uric acid acts on transcription factors as a therapeutic target. Thus, uric acid activates the nuclear factor erythroid 2-related factor2/heme oxygenase 1 (Nrf2/HO-1) pathway and has a positive regulation in the expression of brain-derived neurotrophic factor (BDNF), and nerve growth factor (NGF).

In adult rat, administration of uric acid 24 hours before occlusion of the middle cerebral artery or 1 hour after reperfusion significantly reduces resulting cerebral infarction, suppresses accumulation of reactive oxygen species and decreases lipid peroxidation (Yu Z F, et al. *Uric acid protects neurons against excitotoxic and metabolic insults in cell culture, and against focal ischemic brain injury in vivo*; J Neurosci Res 1998; 53: 613-25). Uric acid administration is neuroprotective in a rat thromboembolic model of focal cerebral ischemia and this neuroprotective effect is synergistic with respect to the beneficial effect achieved by rtPA (Romanos E, Planas A M, Amaro S, Chamorro A. *Uric acid reduces brain damage and improves the benefits of rt-PA in a rat model of thromboembolic stroke*. J Cereb Blood Flow Metab. 2007; 27:14-20).

There are studies that evidence relationship between higher uric acid levels in the blood at the time of a cerebral infarction and the lower neurological severity caused by it.

Additionally, the recent URICO-ICTUS study (phase 2b/3 clinical study) showed that the use of uric acid in combination with standard thrombolytic treatment (alteplase) is safe. In any case, combined therapy in this study did not show statistically significant effect, so conclusion of the study is that no significant change was observed in proportion of patients with excellent results at 90 days (Chamorro A, Amaro S, Castellanos M, Segura T, Arenillas J, Marti-Fábregas J, Gállego J, Krupinski J, Gomis M, Cánovas D, Carné X, Deulofeu R, Román L S, Oleaga L, Torres F, Planas A M; URICO-ICTUS Investigators. *Safety and efficacy of uric acid in patients with acute stroke (URICO-ICTUS): a randomized, double-blind phase 2b/3 trial*. Lancet Neurol. 2014; 13:453-60).

On the other hand, PCT patent application WO2010112113A1 discloses the combined use of uric acid and citicoline for the treatment of stroke, demonstrating its effects in ischemic model cell cultures.

Additionally, the PCT patent application WO2018206826A1 demonstrates the usefulness and efficacy of uric acid for the treatment of cerebral infarction in patients treated by mechanical thrombectomy.

Despite the above, it should be noted that the use of uric acid as a therapeutic agent presents a series of problems that limit its use. On the one hand, uric acid has limited solubility with a tendency to crystallize, which complicates the logistics of its use as a pharmaceutical formulation. On the other hand, the presence of high levels of free uric acid in blood (normally excreted via the kidneys) is usually the cause of the appearance of kidney stones and gout processes, due to the accumulation of urate crystals.

On the other hand, uric acid in the blood has a limited capacity to cross the blood-brain barrier and access the brain parenchyma.

An alternative to the use of free uric acid as a therapeutic agent is the use of therapeutic agents transport systems or platforms (nanomaterials) and controlled release (TLCs), which facilitate solubilization and stability in solution of uric acid (stability of pharmaceutical formulations, allowing adequate logistics for its use in the clinical setting) and its administration to the body in therapeutically relevant doses without exceeding pathological limits of free uric acid in blood. In the state of the art, such solutions for uric acid have not yet been described.

Therefore, given what has been explained above, in the state of the art there is still a need for systems or transport platforms and controlled release (TLCs) for uric acid, which facilitate: solubilization and stability in solution of said uric acid; its administration to the body in therapeutically relevant doses without exceeding pathological limits of free uric acid in the blood; and that allow or facilitate uric acid to cross the blood-brain barrier.

The inventors of the present invention, after extensive and exhaustive experiments, have managed to generate liposomes that effectively encapsulate uric acid and that consequently allow solving the problems and needs present in the state of the art and described above:

1) Facilitate preparation of time-stable uric acid solutions under normal storage conditions.
2) Facilitate controlled and sustained release of therapeutic doses of uric acid into the bloodstream after intravenous administration.
3) Facilitate transfer of uric acid through the blood-brain barrier for its release in the brain parenchyma.
4) Exceed solubility of free uric acid.
5) Improved uric acid stability.
6) Greater ease in synthesis or manufacture of uric acid.

Additionally, inventors of the present invention have discovered processes for the manufacture of said uric acid encapsulating liposomes. Finally, as will be apparent from examples included herein liposomes with encapsulated uric acid have been shown to be more effective in treating stroke than free uric acid.

DETAILED DESCRIPTION

Therefore, in a first aspect, the present invention relates to liposomes that encapsulate uric acid (and/or uric acid salts, derivatives and precursors).

In a second aspect, the present invention relates to a process for the manufacture of liposomes of the present invention.

In a third aspect, the present invention relates to liposomes that encapsulate uric acid (and/or uric acid salts, derivatives and precursors) obtained by the process for the manufacture of liposomes of the present invention.

In a further aspect, the present invention relates to a pharmaceutical composition comprising the present invention liposomes.

In a fifth aspect, the present invention provides a pharmaceutical composition or liposomes, both according to the present invention, for use as a medicine, more preferably for use in prevention, amelioration and/or treatment of a cerebrovascular disease, even more preferably for use in prevention, amelioration and/or treatment of stroke.

In a sixth aspect, the present invention relates to use of a pharmaceutical composition or liposomes, both according to the present invention, for the preparation of a medicament for prevention, improvement and/or treatment of a neurovascular disease, even more preferably for prevention, improvement and/or treatment of stroke.

In a final aspect, the present invention refers to a prevention method, improvement and/or treatment of a neurovascular disease (preferably, stroke) in a patient in need thereof, which comprises the administration of a pharmaceutical composition or liposomes, both according to the present invention, to said patient.

As used herein, "cerebral infarction", "stroke" and "cerebrovascular accident" are used interchangeably, interchangeably and equivalently and refer to any pathology or clinical situation that implies that a part of the brain is left without blood irrigation.

As used herein, "uric acid salts" mention includes the pharmaceutically acceptable salts of said uric acid. The reference to uric acid salts can be a reference to a uric acid salt or to a combination of different uric acid salts. Uric acid salt or salts refer to both different counterions (for example, Na, Li or K) as well as different protonation states of uric acid, which determines that there are monobasic salts and dibasic salts.

As used herein, "uric acid derivatives" takes on the meaning that it commonly has in the state of the art. Reference to "uric acid derivatives" may be a reference to an uric acid derivative or a combination of different uric acid derivatives, including, but not limited to, minor structural modifications in molecular formula of uric acid that do not affect its biological activity but can improve the way in which the compound is absorbed, distributed, metabolized and/or excreted. More preferably, "uric acid derivatives" refer to N-mono-, N-di-, N-tri- and/or N-tetra substituted derivatives, with alkyl chains as substituents for uric acid nitrogens. Examples of these "uric acid derivatives" appear in Fraisse L, et al. *Long-chain-substituted uric acid and 5,6-diaminouracil derivatives as novel agents against free radical processes: synthesis and in vitro activity*. J Med Chem. 1993 May 14; 36(10):1465-73. doi: 10.1021/jm00062a020. Erratum in: J Med Chem 1993 Sep. 17; 36 (19): 2832. PMID: 8496914.

As used herein, "uric acid precursors" includes or refers to any formulation or chemical form that, once administered to a patient, is metabolized (i.e., converted within the body), providing uric acid (as such or in its dissociated form), a monobasic uric acid salt (as such or in its dissociated form), a dibasic uric acid salt (as such or in its dissociated form) or urate. The reference to uric acid precursors can be a reference to a uric acid precursor or to a combination of different uric acid precursors.

As used herein, "patient" and its plural are used to refer to mammals, preferably humans, suffering from stroke, regardless of their sex and age and regardless of whether they have other pathologies (diagnosed or not).

As used herein, "liposome" and its plural acquire the meaning that they commonly have in the state of the art, that is, they are small artificial vesicles of spherical shape that can be created from cholesterol and non-toxic natural phospholipids. Liposomes have a simultaneous hydrophobic and hydrophilic character, and their hydrodynamic diameter can vary from 25 to 2500 nm (0.025 to 2.5 µm). Based on their size and bilayers number that form them, liposomes can also be classified into: (1) multilamellar vesicles (MLV) and (2) unilamellar vesicles. Unilamellar vesicles, in turn, can be classified into: (1) large unilamellar vesicles (LUV) and (2) small unilamellar vesicles (SUV).

As used herein, "hydrodynamic diameter" takes on the meaning that it commonly has in the state of the art. Whenever this variable is mentioned herein, it is measured using the DLS (Dynamic Light Scattering) technique, carried out in water at a temperature of 25° C.

Therefore, as indicated above, in a first aspect, the present invention relates to liposomes that encapsulate uric acid, uric acid salts, uric acid derivatives, uric acid precursors or combinations thereof.

In the most preferred embodiment, the present invention relates to liposomes that encapsulate uric acid.

In a preferred embodiment, the liposomes of the present invention encapsulate between $6*10^{-20}$ and $6*10^{-18}$ uric acid moles, uric acid salts, uric acid derivatives, uric acid precursors or combinations thereof (preferably uric acid) per liposome, more preferably $6.24*10^{-19}$ uric acid moles, uric acid salts, uric acid derivatives, uric acid precursors or combinations thereof (preferably uric acid) per liposome.

Additionally, liposomes of the present invention can be any type of liposome known in the state of the art. More preferably, liposomes of the present invention are unilamellar liposomes, even more preferably small unilamellar vesicles (SUV).

Also preferably, liposomes of the present invention have a hydrodynamic diameter of between 80 and 140 nm, more preferably 110 nm. Said hydrodynamic diameter is obtained by the DLS (Dynamic Light Dispersion) technique, carried out in water at a temperature of 25° C.

In a preferred embodiment, liposomes of the present invention have a phase transition temperature higher than 45° C., more preferably a phase transition temperature between 45° C. and 70° C., even more preferably a phase transition temperature higher than 45° C. and lower than 70° C., even more preferably a phase transition temperature of 55° C. Also preferably, liposomes of the present invention have a positive surface charge, more preferably zeta potential of liposomes of the present invention is greater than 0 mV and less than 15 mV, even more preferably 10 mV. Said zeta potential is obtained using a DLS (Dynamic Light Dispersion) equipment, measuring in water at a temperature of 25° C.

Liposomes of the present invention have a lipid bilayer with a suitable composition to allow liposomes synthesis and stability, for encapsulation of uric acid and for its release (preferably, at the site of interest, more preferably in the brain and, preferably in a sustained way over time). In a preferred embodiment, liposomes of the present invention comprise positively charged double chain phospholipids and cholesterol. Therefore, preferably, liposomes of the present invention are unilamellar and present a lipid bilayer that encapsulates uric acid, said lipid bilayer comprising double-chain phospholipids and at least one positively charged cholesterol derivative (more preferably, said lipid bilayer consisting of double chain phospholipids and at least one positively charged cholesterol derivative).

Preferably, the at least one positively charged cholesterol derivative is a positively charged cholesterol derivative. More preferably, the positively charged cholesterol derivative is dimethylaminoethane-carbamoyl-cholesterol hydrochloride (Dimethylaminoethane-Carbamoyl-cholesterol (3β-[N—(N',N'-dimethylaminoethane)-carbamoyl] cholesterol hydrochloride, hereinafter DC-cholesterol).

Preferably, double-chain phospholipids comprise a combination of phospholipids having one or more chains of a long-chain polymer that hinder liposomes opsonization (opsonin binding to liposome) in blood (more preferably, a linked chain to its polar head) and phospholipids that do not have polyethylene glycol attached to its polar head. In a preferred embodiment, in the liposomes of the present invention:

between 2.5% and 10% molar of the double-chain phospholipids are phospholipids with one or more chains of a long-chain polymer that hinder liposomes opsonization in blood attached to their polar head; more preferably, 7.5% molar of double-chain phospholipids are phospholipids with long-chain polymer chains that hinder liposomes opsonization in blood; and the rest of the double-chain phospholipids are phospholipids without polyethylene glycol attached to their polar head, that is, between 90 and 97.5% molar of the double chain phospholipids are phospholipids without polyethylene glycol attached to their polar head, more preferably 92.5% mol are phospholipids without polyethylene glycol attached to its polar head.

Long chain polymer that hinders liposomes opsonization in blood is preferably selected from: polyethylene glycol (PEG), Polyoxazolines (POX), Polyvinylpyrrolidinones (PVP), Polyglycerols (PG), Polyacrylamides (PAA, NIPAM, PHPMA, PNIPAM), Polysaccharides, Polyaminoacids or combinations thereof, more preferably the Long-chain polymer that hinders liposomes opsonization in blood is polyethylene glycol.

Preferably, in double-chain phospholipids with one or more polyethylene glycol chains attached to their polar head (more preferably, a polyethylene glycol chain attached to its polar head), each of polyethylene glycol chains has a molecular weight of between 1000 and 5000 Da, more preferably a molecular weight of 2000 Da.

Also preferably, double chain phospholipids with one or more polyethylene glycol chains attached to their polar head (more preferably, a polyethylene glycol chain attached to their polar head) are selected from 16:0 PEG2000 PE (or 1,2 dipalmitoyl-sn-glycero-3-phosphoethanolamine-N-[methoxy (polyethylene glycol)-2000]), 18:0 PEG2000 PE (or 1,2-distearoyl-sn-glycero-3-phosphoethanolamine-N-

[methoxy (polyethylene glycol)-2000]), 18:0 PEG5000 PE (or 1,2-distearoyl-sn-glycero-3-phosphoethanolamine-N-[methoxy (polyethylene glycol)-5000]) or combinations thereof. In the most preferred embodiment, double-chain phospholipids with one or more polyethylene glycol chains attached to their polar head (more preferably, a polyethylene glycol chain attached to its polar head) are selected from 16:0 PEG2000 PE, 18:0 PEG2000 PE, or combinations thereof, even more preferably, double chain phospholipids with one or more polyethylene glycol chains attached to their polar head (more preferably, a polyethylene glycol chain attached to their polar head) are 18:0 PEG200 PE.

Double-chain phospholipids without polyethylene glycol attached to its polar head are preferably phospholipids derived from phosphatidylcholine, neutral (zwitterionic) and each of its two chains having 16 to 18 carbon units. More preferably, double chain phospholipids without polyethylene glycol attached to its polar head are selected from DSPC (18:0 PC or 1,2-distearoyl-sn-glycero-3-phosphocholine), DPPC (16:0 PC or 1,2-dipalmitoyl-sn-glycero-3-phosphocholine)), 17:0 PC (or 1,2-diheptadecanoyl-sn-glycero-3-phosphocholine) or combinations thereof. In the most preferred embodiment, double chain phospholipids without polyethylene glycol attached to its polar head are DSPC.

Preferably, in liposomes of the present invention, molar fraction ratio between double chain phospholipids and positively charged cholesterol (preferably DC-cholesterol) is between 0.6:0.4 and 0.75:0.25, more preferably, molar fraction ratio of double chain phospholipids to positively charged cholesterol (preferably DC-cholesterol) is 0.667: 0.333.

Therefore, in the most preferred embodiment, in liposomes of the present invention, their membrane (lipid bilayer) consists of DSPC:DC-Cholesterol: 18:0 PEG2000-PE with a ratio, in molar fractions, of 0.617:0.333:0.050.

Preferably, liposomes of the present invention are stable at room temperature for at least 5 days, more preferably, at least 7 days, more preferably, at least 12 days, more preferably at least 15 days, even more preferably at least 21 days. In this period of time, liposomes conserve at least 80% of encapsulated uric acid in relation to encapsulated uric acid that initially presented.

As derived from obtained results in examples included herein, liposomes of the present invention make it possible to solve the problems present in the state of the art and, consequently:

1) They facilitate preparation of time-stable uric acid solutions under normal storage conditions (at least 21 days at room temperature without signs of precipitation and keeping the transparence of the preparation).

2) They facilitate handling and conservation of uric acid.

3) They facilitate or allow controlled and sustained release of therapeutic doses of uric acid into the bloodstream after intravenous administration.

4) They facilitate transfer of uric acid through the blood-brain barrier for its release in the brain parenchyma.

5) They allow to overcome solubility of free uric acid.

6) They allow to improve stability of uric acid.

7) They provide ease in the synthesis or manufacture of uric acid.

8) They provide a superior therapeutic effect compared to the use of free uric acid.

In a second aspect, as indicated above, the present invention relates to a process for preparation or manufacture of liposomes that encapsulate uric acid, uric acid salts, uric acid derivatives, uric acid precursors or combinations of the same (more preferably uric acid), comprising the steps of:

a) Form a lipid film;

b) Rehydrate the lipid film formed in step a) to obtain liposomes;

c) Extrude obtained liposomes in step b); and d) Filter obtained liposomes in step c), characterized in that:

Steps a) to d) are carried out free of calcium ions;

A lithium and/or potassium ions solution (preferably at a concentration of at least 0.15 mM, even more preferably 0.15 mM) is used, preferably at pH 7.2-7.4, which is used as an aqueous solvent, in all the stages of the process that require it;

A lithium and/or potassium ions solution (preferably at a concentration of at least 0.15 mM, even more preferably 0.15 mM), preferably at pH 7.2-7.4 is used, for cleaning used material in the method and/or sterile material is used, in all stages of the method;

To rehydrate lipid film, in step b), an uric acid aqueous solution, uric acid salts, uric acid derivatives, uric acid precursors or combinations thereof (more preferably uric acid) is used; comprising uric acid, uric acid salts, uric acid derivatives, uric acid precursors or combinations thereof (more preferably uric acid); and lithium and/or potassium ions in an amount that is at least twice that of uric acid, uric acid salts, uric acid derivatives, uric acid precursors or combinations thereof (more preferably uric acid), and such preparation comprises:

1—preparing a lithium and/or potassium ions solution: dissolving appropriate amount of lithium and/or potassium ions (preferably a lithium or potassium salt or a combination of lithium and/or potassium salts) in a suitable solvent (preferably double distilled and deionized water or HPLC—high performance liquid chromatography—purity water; even more preferably HPLC purity water);

2—once the lithium and/or potassium ion solution has been prepared, pH is adjusted to a value between 10 and 11;

3—then, necessary amount of uric acid, uric acid salts, uric acid derivatives, uric acid precursors or combinations thereof (more preferably uric acid) is added, continuously monitoring pH of solution so that during the addition of uric acid it is kept in the range 10-11 at all times.

4—at the end of all acid, salts, derivatives, precursors or combinations thereof dissolution, pH is lowered (preferably very slowly) to a value between 7.2 and 7.4.

In extrusion step c), a lithium and/or potassium ions solution (preferably, at a concentration of at least 0.15 mM, even more preferably 0.15 mM) is used as solvent; and In filtration step d) a lithium and/or potassium ions solution (preferably, at a concentration of at least 0.15 mM, even more preferably 0.15 mM) is used as solvent, which is adjusted to required volume and preferably at pH 7.2-7.3.

In step a) of the process of the present invention, lipid bilayer is formed using desired or suitable lipid components, that is, it is formed using the desired components for the lipid bilayer of the liposomes. In this sense, in relation to lipid bilayer and its composition, everything indicated above in the first aspect of the present invention applies.

In extrusion step c), liposomes are extruded so that desired size liposomes are obtained, more preferably, liposomes are passed (extruded) through extrusion membranes with the appropriate pore size to obtain liposomes of the size wanted. Preferably, extrusion is carried out serially from larger pore size membranes to smaller pore size membranes until the desired liposome size is reached. For example, and preferably, twice through 0.4-micron pore size membranes (preferably polycarbonate), then 4 times using a 0.2-micron pore size membrane (preferably polycarbonate), and finally 8 times using a 0.1-micron pore size membrane (preferably polycarbonate) to obtain nominal size liposomes (hydrodynamic diameter) around 100 nanometers (0.1 microns).

In filtration step d), components not incorporated in liposomes are removed and, if deemed appropriate, the medium can be changed. Step d) can be carried out by any known method in the state of the art, more preferably it is carried out by molecular mass cutting filtration (filtration through membrane by centrifugation) or by dialysis.

In a preferred embodiment, HPLC (high performance liquid chromatography) grade water is used throughout the method.

Also, in a more preferred embodiment of the process of the present invention, the entire process is carried out free of divalent ions.

Additionally, preferably, steps a) to d) of the process of the present invention are carried out sodium and/or carbonate ions free. Most preferably, the entire method is carried out sodium and carbonate ions free.

In the process of the present invention, also preferably, uric acid aqueous solution, uric acid salts, uric acid derivatives, uric acid precursors or combinations thereof (more preferably uric acid) used to rehydrate lipid film formed in step a) comprises 20 mM uric acid, uric acid salts, uric acid derivatives, uric acid precursors or combinations thereof (more preferably 20 mM uric acid) and at least 40 mM lithium and/or potassium ions (more preferably 40 mM lithium ions).

On the other hand, in the process of the present invention, where lithium and/or potassium ions are indicated, lithium ions are preferably. Most preferably, lithium ions are provided in the form of lithium chloride.

In a preferred embodiment of the process of the present invention, after step d), process comprises a step of medium substitution in which liposomes are dissolved.

In another preferred embodiment of the process of the present invention, after step d), process comprises a lyophilization step. Also preferably, after lyophilization step, the process of the present invention comprises a reconstitution step.

In a more preferred embodiment, in the process of the present invention all steps are carried out calcium ions free.

In everything not detailed above, the process of the present invention is as liposomes manufacture or preparation processes of the state of the art.

Therefore, preferably the liposomes manufacture or preparation process that encapsulate uric acid, uric acid salts, uric acid derivatives, uric acid precursors or combinations thereof (more preferably uric acid) of the present invention comprises:

Phase 1: Lipid Film Formation:
  1) Allow reagents to reach room temperature.
  2) Clean the material to be used or use sterile material.
  3) Dry glassware to be used (preferably under a nitrogen or argon gas stream).
  4) Weigh required amount of double-chain phospholipids and positively charged cholesterol (according to explained above in the first aspect of the present invention) and dissolve them in an organic solvent (preferably, in a $CH_3Cl$:MeOH (chloroform-methanol, 6:1)) mixture.

5) Place obtained solution in step 4 on a rotary evaporator and completely evaporate the organic solvent (preferred working conditions are: bath at 30° C., rotation speed of about 140 rpm (revolutions per minute) and controlled pressure drops up to 200 mbar (20 kPa), and from this point on, reduce the pressure very slowly (or increase the vacuum very slowly) to the minimum possible over a period of 10 minutes).
  Is very important that once the solvent evaporates, a homogeneous lipid film remains at the bottom of the used container (preferably frosted pear-shaped flask). If not, it will be necessary to repeat steps 4 and 5 above.
  6) Hold the container with step 5 film (preferably frosted pear-shaped flask) at maximum vacuum for at least 15 minutes.
  7) Break the vacuum slowly and place the container for a minimum of 1 hour under stream of gas (preferably nitrogen or argon) or keep it in a high vacuum desiccator for between 12 and 24 hours, to favor total evaporation of organic solvents.

Phase 2: Lipid Film Rehydration
  8) Heat aqueous solvent to be used above the phase transition temperature of used lipids (65° C. in the case of liposomes lipids of the present invention), maintaining this temperature (hereinafter, working temperature) during all the process. In this step an uric acid aqueous solution, uric acid salts, uric acid derivatives, uric acid precursors or combinations thereof (more preferably uric acid) is used; comprising uric acid, uric acid salts, uric acid derivatives, uric acid precursors or combinations thereof (more preferably uric acid); and lithium and/or potassium ions in an amount that is at least twice that of uric acid, uric acid salts, uric acid derivatives, uric acid precursors or combinations thereof (more preferably uric acid), and such preparation comprises:
    a) preparing a lithium and/or potassium ions solution: dissolving appropriate amount of lithium and/or potassium ions (preferably a lithium or potassium salt or a combination of lithium and/or potassium salts) in a suitable solvent (preferably double distilled and deionized water or HPLC—high performance liquid chromatography—purity water; even more preferably HPLC purity water); once the lithium and/or potassium ion solution has been prepared, pH is adjusted to a value between 10 and 11 using;
    b) then, necessary amount of uric acid, uric acid salts, uric acid derivatives, uric acid precursors or combinations thereof (more preferably uric acid) is added, continuously monitoring pH of solution so that during the addition of uric acid it is kept in the range 10-11 at all times.
    c) at the end of all acid, salts, derivatives, precursors or combinations thereof dissolution, the pH is lowered very slowly to a value between 7.2 and 7.4.
  9) Heat extrusion system to the same temperature as in step 8.
  10) Heat the container with the obtained lipid film in step 7 until reaches the working temperature (temperature indicated in step 8) (preferably, placing the container in water bath) and then add the appropriate amount of aqueous solvent prepared in step 8, and shake until complete dissolution of the film (the process can be facilitated by adding a few units of glass beads of about 3 mm in diameter). Maintain stirring for about 10 min, with the container always at working temperature (preferably, always in the bath).

Phase 3: Liposome Extrusion

11) With extruder balanced at working temperature, wash it 3 times with a generous amount of aqueous solvent and extrude the obtained mixture in step 10 using one or more membranes with appropriate pore size depending on the wanted liposomes size.

Phase 4: Liposome Filtration

12) Filter extruded solution in step 11) through filtration systems with cut by molecular mass or through dialysis processes.

As stated above:

The entire method is carried out calcium ions free (and, preferably, the entire method is also carried out sodium and carbonate ions free).

A lithium and/or potassium ions solution (preferably at a concentration of at least 0.15 mM, even more preferably 0.15 mM) is used, preferably at pH 7.2-7.4, which is used as an aqueous solvent, in all the stages of the process that require.

A lithium and/or potassium ions solution (preferably at a concentration of at least 0.15 mM, even more preferably 0.15 mM), preferably at pH 7.2-7.4 is used, for cleaning used material in the method and/or sterile material is used, in all stages of the.

In extrusion phase 3, a lithium and/or potassium ions solution (preferably, at a concentration of at least 0.15 mM, even more preferably 0.15 mM) is used as solvent; and In filtration phase 4, a lithium and/or potassium ions solution (preferably, at a concentration of at least 0.15 mM, even more preferably 0.15 mM) is used as solvent, which is adjusted to required volume and preferably at pH 7.2-7.3.

All preferred embodiments explained above for the process of the present invention apply in this case.

Preferably, step 11 indicated above comprises:

a) Assemble a 0.4 microns pore size membrane (preferably polycarbonate) in the extruder and wet it with solvent (preferably, the same solvent as that used in lipid film rehydration phase 2, that is, lithium and/or potassium ion dissolution).

b) Fill the extruder with the obtained aqueous mixture in step 10 and allow the temperature to equilibrate at a temperature higher than the phase transition temperature of the liposomes lipids of the present invention (preferably at 65° C. and preferably approximately 10 min).

c) Using gas stream (preferably nitrogen or argon) to force extrusion of aqueous mixture through the membrane. The sample is collected in a hot container, at working temperature (preferably, working temperature should never be lost).

d) Repeat extrusion process on the 0.4-micron membrane (steps 12 to 14).

e) Repeat the process (preferably 4 times) now using a 0.2-micron pore size membrane (preferably polycarbonate).

f) Repeat extrusion process (8 times) using a 0.1-micron pore size membrane (preferably polycarbonate) to obtain nominal size liposomes (hydrodynamic diameter) around 100 nanometers (0.1 microns).

Results evident that a person skilled in the art will be able to adjust membrane sizes and repeats during extrusion in order to obtain the desired size liposomes.

In phase 4, individual components that have not been integrated into liposomes are eliminated and their final concentration is adjusted (adjustment of the final volume of solution) and it is possible, if desired, to change aqueous solvent used for preparation of liposomes by another solvent of a hydrophilic nature (for example, by saline). In a preferred embodiment, therefore, step 12 of the process of the present invention comprises:

a) Fill with solvent (preferably, the same solvent as that used in phase 2 of lipid film rehydration, that is to say, lithium and/or potassium ions solution) a tube (preferably a centrifugal filtration unit) with cut-off membrane of 30 kDa and filter it in a centrifuge (preferably 2 hours at 6000 g at room temperature). Preferably, this filtering should be carried out 3 times.

b) Pass the extruded liposome solution obtained in step 11 to centrifugal filtration unit previously washed, and centrifuge (preferably, 2 hours at 6000 g).

c) Adjust final volume of liposome solution to the desired value (for example, 10 mL) and adjust the pH to the desired value (preferably 7.2-7.4), preferably using HCl (1N) or NaOH (1N).

As can be seen in examples included herein, process of the present invention allows the correct liposomes manufacture by encapsulating uric acid, uric acid salts, uric acid derivatives, uric acid precursors or combinations thereof (more preferably uric acid) in 100% of cases, preventing precipitates from appearing and providing stable liposomes over time at room temperature (at less for 21 days and conserving 80% of encapsulated uric acid). Additionally, and surprisingly, liposomes obtained by the method of the present invention have a greater therapeutic effect than liposomes obtained by the method of the state of the art.

In a third aspect, the present invention relates to liposomes that encapsulate uric acid, uric acid salts, uric acid derivatives, uric acid precursors or combinations thereof (preferably uric acid) obtained by the method of the present invention (explained in the second aspect of the present invention).

Preferred embodiments and explanations given in the first and second aspects of the present invention are applicable to this third aspect of the present invention (with the necessary adaptations).

In a fourth aspect, as indicated above, the present invention refers to a pharmaceutical composition comprising liposomes according to first aspect of the present invention and/or obtained liposomes according to the process of the present invention (method explained in the second aspect of the present invention).

Preferably, pharmaceutical composition of the present invention comprises a uric acid, uric acid salts, uric acid derivatives, uric acid precursors or combinations thereof (preferably uric acid) concentration therapeutically effective, more preferably between 0.5 and 10 mg/mL, more preferably 1.6 mg/mL.

Also preferably, pharmaceutical composition of the present invention comprises a lipid concentration of between 10 and 2 mM, more preferably between 7 and 4 mM, more preferably between 4.3 and 4.7 mM, even more preferably 4.5 mM.

Is contemplated that pharmaceutical composition of the present invention may be in any form known in the state of the art, provided that said form is compatible with the chosen administration form. Preferably pharmaceutical composition of the present invention is in liquid or lyophilized form, more preferably liquid. In cases wherein pharmaceutical composition of the present invention is in lyophilized form, is contemplated to be reconstituted with a suitable solution or solvent, preferably saline before use.

In a fifth aspect, present invention provides a pharmaceutical composition or liposomes, both in accordance with the present invention, for use as medicine.

Pharmaceutical composition of the present invention is in accordance with what was explained above in the fourth aspect of the present invention.

Liposomes of the present invention are as explained above in the first or third aspect of the present invention.

More preferably, this fifth aspect of the present invention discloses a pharmaceutical composition or liposomes, both according to the present invention, for use in prevention, amelioration and/or treatment of a cerebrovascular disease, even more preferably, for its use in prevention, improvement and/or treatment of stroke.

Is contemplated that said stroke may be ischemic or hemorrhagic, more preferably the stroke is an ischemic stroke, even more preferably an ischemic stroke treated with thrombolytic drugs (e.g., alteplase and/or tenecteplase), an ischemic stroke treated by mechanical thrombectomy, or an ischemic stroke treated with thrombolytic drugs and mechanical thrombectomy. Is contemplated that these treatments (thrombolytic drugs, mechanical thrombectomy and any other stroke treatment that may be considered) may be prior, concurrent or subsequent to the use or administration of the pharmaceutical composition or liposomes of the present invention.

Therefore, the present invention contemplates that the pharmaceutical composition of the present invention or the liposomes of the present invention are used alone or in combination with other compounds (preferably active ingredients). In a preferred embodiment, they are used in combination with a thrombolytic agent, more preferably with a tissue plasminogen activator (hereinafter tPA) (for example, alteplase).

Is also contemplated that the pharmaceutical composition of the present invention or the liposomes of the present invention are used in combination with, for example, citicoline.

In relation to the foregoing, is contemplated that the combined use is within the same composition or that is in the form of at least one additional composition. In the latter case, as indicated above, is contemplated that the pharmaceutical composition or liposomes of the present invention are administered before, at the same time or after the at least one additional composition.

In a preferred embodiment, the pharmaceutical composition or liposomes of the present invention are used in combination with a composition comprising tPA (preferably alteplase) and are used at the same time, that is, they are administered together, even more preferably, first the composition comprising tPA is administered and before the end of the administration thereof, the administration of the pharmaceutical composition or the liposomes of the present invention is started.

The dose of the pharmaceutical composition or liposomes of the present invention is a therapeutically effective dose.

In a preferred embodiment, uric acid, uric acid salts, uric acid derivatives, uric acid precursors or combinations thereof (preferably uric acid) dose is between 10 and 20 mg/kg patient, 16 mg/kg of patient.

In a more preferred embodiment of this fifth aspect of the present invention, administered dose is between 500 and 2000 mg uric acid, uric acid salts, uric acid derivatives, uric acid precursors or combinations thereof (preferably, uric acid), more preferably administered dose is between 500 and 1000 mg uric acid, uric acid salts, uric acid derivatives, uric acid precursors or combinations thereof (preferably uric acid), even more preferably administered dose is 1000 mg uric acid, uric acid salts, uric acid derivatives, uric acid precursors or combinations thereof (preferably uric acid).

The pharmaceutical composition of the present invention and the liposomes of the present invention, in this fifth aspect of the present invention, can be administered by any of the routes known in the state of the art. In a preferred embodiment, the pharmaceutical composition of the present invention and the liposomes of the present invention are administered intravenously.

The treatment is administered to a patient in need thereof, and said patient is in accordance with the above.

In a sixth aspect, the present invention relates to use of a pharmaceutical composition or liposomes, both according to the present invention, for the preparation of a medicament for prevention, improvement and/or treatment of a cerebrovascular disease.

In a preferred embodiment, cerebrovascular disease is stroke.

Embodiments explained in the fifth aspect of the present invention apply directly (with necessary adaptations) to this sixth aspect of the present invention.

In a final aspect, the present invention refers to a prevention method, improvement and/or treatment of a cerebrovascular disease in a patient in need thereof, which comprises the administration of a pharmaceutical composition or liposomes, both according to the present invention, to said patient.

In a preferred embodiment, cerebrovascular disease is stroke.

Embodiments explained for the fifth aspect of the present invention apply directly (with necessary adaptations) to this final aspect of the present invention.

To enable a better understanding, the present invention is described below in more detail with reference to the accompanying figures, which are filed by way of example, and with reference to the illustrative and non-limiting examples included below.

FIG. 1 shows the liposomes stability of the present invention over time when stored at room temperature, as indicated in Example 2 included below. FIG. 1 shows the uric acid percentage that remains encapsulated in the liposomes of the present invention at different time intervals, as a measure of stability of said liposomes. In this sense, a 100% value is established for encapsulated uric acid in liposomes on day 1 and the result for the rest of days is indicated based on or compared to the value on day 1. On y-axis, encapsulated uric acid in liposomes percentage is indicated (considering as 100% the amount of encapsulated uric acid in the liposomes on day 1). x-axis shows the time (storage) in days since the start of the experiment.

Figure 2:
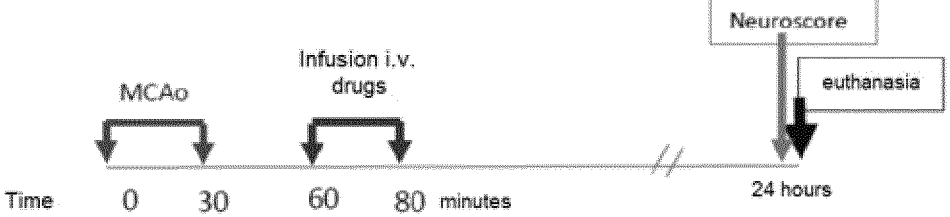

FIG. 2 shows the experimental scheme of the first experiment included in Example 4 below.

Figure 3:
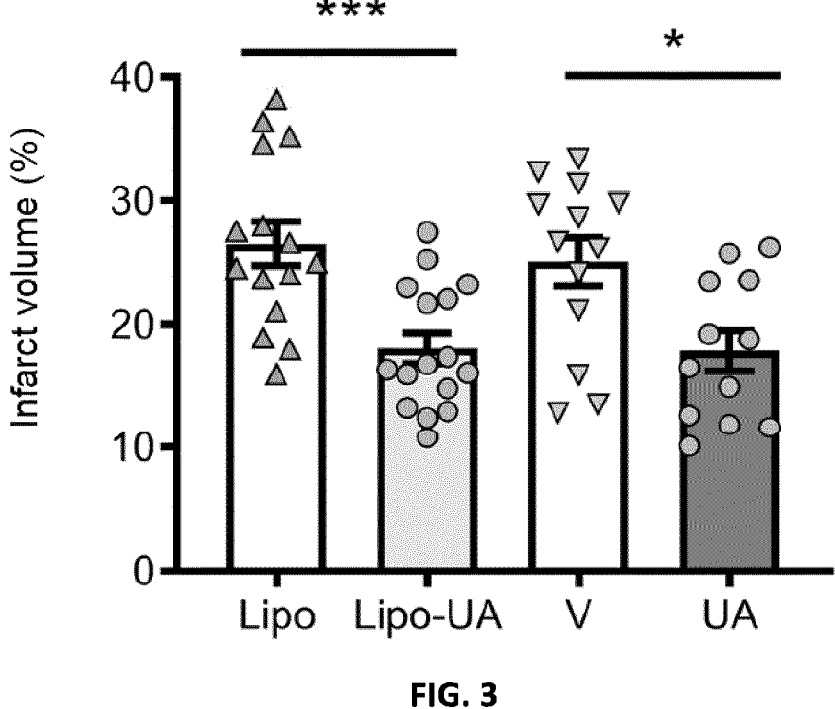

FIG. 3 shows the volume of cerebral infarction (in percentage with respect to volume of the corresponding hemisphere (corrected for edema)) obtained in the first experiment mentioned in example 4. y-axis reflects the volume of cerebral infarction (in percentage with respect to volume of the corresponding hemisphere (corrected for edema)) and x-axis shows the different experimental groups, from left to right, as indicated in example 4: Lipo (empty liposomes diluted in saline), Lipo UA (Liposomes according to the present invention, i.e., that encapsulate uric acid), V (vehicle) and UA (free uric acid solution).

Figure 4:
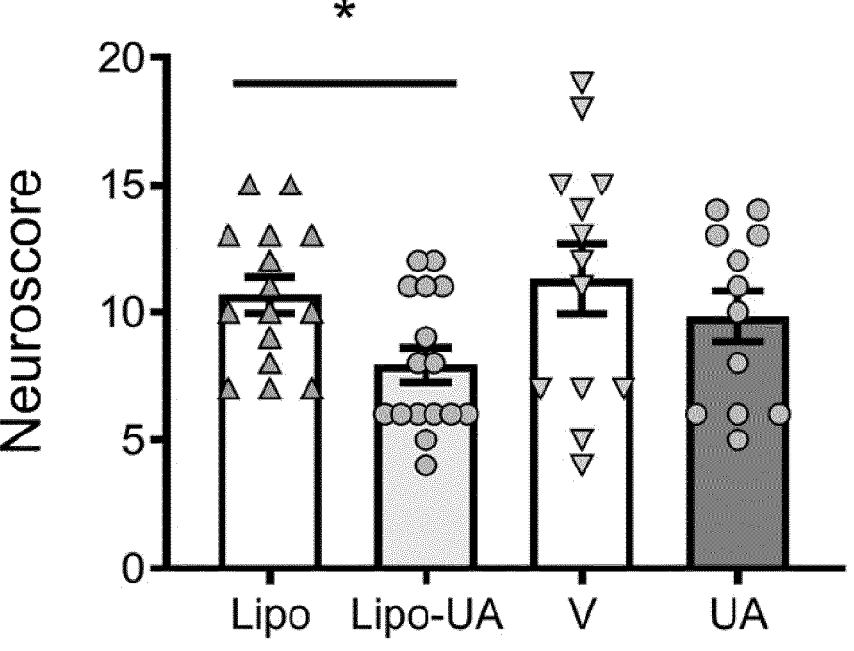
Figure 5A:
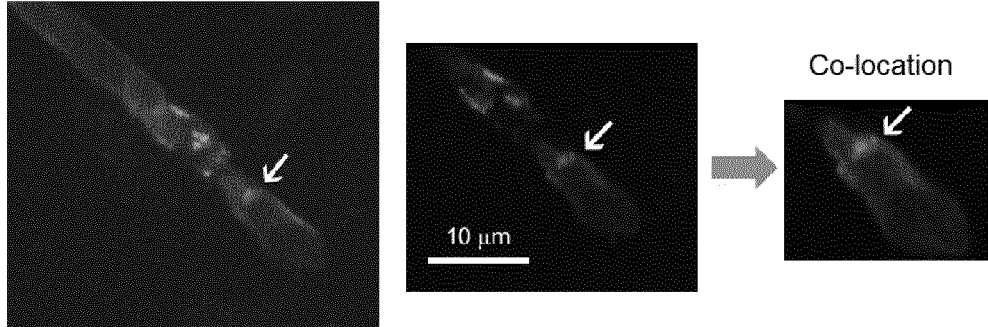
Figure 5B:
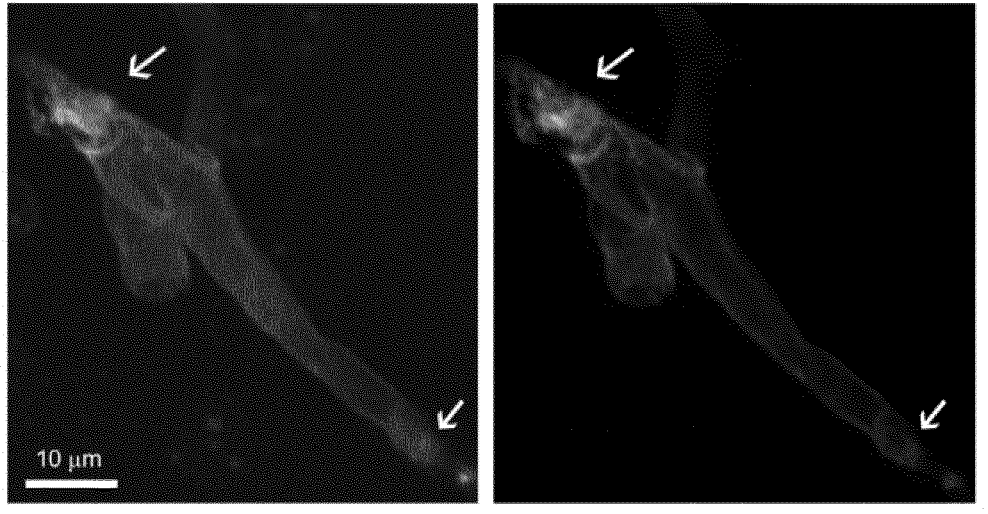
Figure 5C:
Figure 5C:
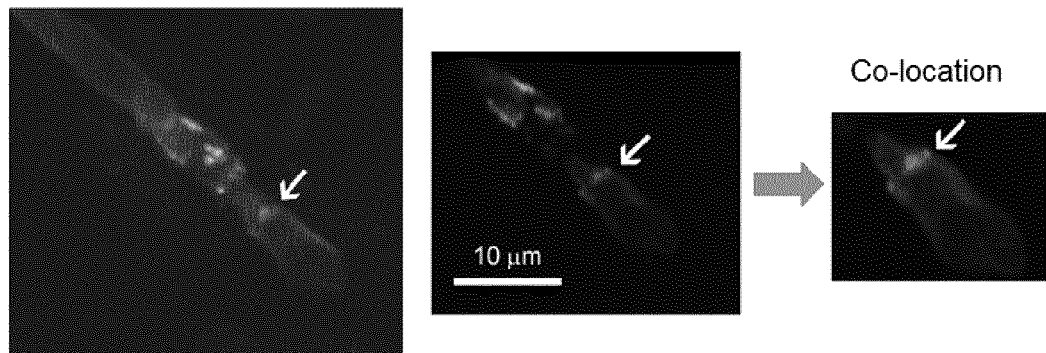
Figure 5D:
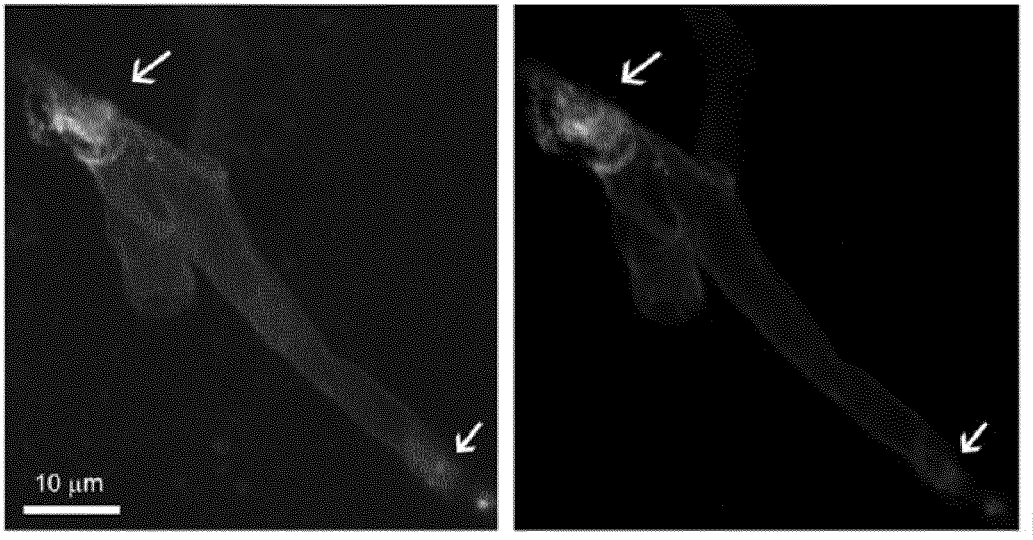

FIG. 4 shows the result of the neurological tests (neuroscore) obtained in the first experiment mentioned in example 4. y-axis reflects the neuroscore and x-axis shows the different experimental groups, from left to right, as indicated in example 4: Lipo (empty liposomes diluted in saline), Lipo UA (Liposomes according to the present invention, i.e., that encapsulate uric acid), V (vehicle) and UA (free uric acid solution).

FIG. 5 shows fluorescence confocal microscopy images obtained in Example 5 of mouse ischemic brains. In FIGS. 5A and 5B images, cell nuclei are shown in blue, cerebral blood vessels in red and liposomes of the present invention in green. Is observed that the liposomes of the present invention co-localize or localize in the cerebral vessels of mice. In both FIG. 5A and FIG. 5B, the dates show the co-localization areas of liposomes and cerebral blood vessels. The corresponding images on the right in both FIGS. 5A and 5B show in gray the cerebral liposomes and blood vessels co-localization zone as calculated by image analysis with the ImageJ Fiji program. FIG. 5C is the same as FIG. 5A but in black and white. FIG. 5D is the same as FIG. 5B but in black and white.

EXAMPLES

Example 1. Preparation Liposomes Method by Encapsulating Uric Acid, Comparison of the State of the Art Method for the Preparation of Liposomes with the Method of the Present Invention a) State of the Art Method for Liposomes Preparation (See, for Example, Mulder W J, Strijkers G J, Van Tilborg G A et al. Lipid-Based Nanoparticles for Contrast-Enhanced MRI and Molecular Imaging. NMR Biomed. 2006; 19 (1): 142-64; Needle J, Brea D, Arqibay B, et al. Quick Adjustment of Imaging Tracer Payload, for In Vivo Applications of Theranostic Nanostructures in the Brain. Nanomedicine. 2014; 10(4):851-8). "Stealth or Silent" or "Long Circulating Blood Time" Liposomes Preparation Based on DSPC and Cholesterol For the preparation of DSPC liposomes (18:0 PC, or 1,2-distearoyl-sn-glycero-3-phosphocholine), PEG2000-PE (1,2-distearoyl-sn-glycero-3-phosphoethanolamine-N-[methoxy (polyethylene glycol)-2000) and cholesterol are used in the amounts indicated in table 1, aiming at the preparation of liposomes containing a lipids total amount of 25 μmol (normally between 25-100 μmol are prepared).

TABLE 1

Molecular weight, molar fraction and total amount of each of the liposome components to obtain 25 μmol of liposomes in the liposome manufacturing process of the state of the art.

| components | Molecular weight (g/mol) | Amount (mg) | Molar fraction |
|---|---|---|---|
| DSPC (18:0 PC) | 790.1 | 12.18 | 0.617 |
| 18:0 PEG2000 PE | 2805.5 | 3.51 | 0.050 |
| Cholesterol | 386.6 | 3.22 | 0.333 |

All these components are commercially available (for example, from Avanti Polar Lipids with references 850365P, 880120P and 700001P).

The method carried out, briefly, was:

Phase 1: Lipid Film Formation
1) Remove the reagents from the freezer (stored at −20° C.) and allow them to reach room temperature before opening the containers that contain them.
2) Clean a reaction flask (preferably pear-shaped) with milliQ water or similar (3×), followed by ethanol (3×)

and acetone (3×). Clean in the same way a rotary evaporator and any other non-disposable glassware that needs to be used.
3) Dry the glassware to be used under nitrogen or argon gas stream.
4) Weigh the lipids and cholesterol required amount (see table 1), transfer them to the reaction flask and add 7 mL of $CH_3Cl$:MeOH (chloroform-methanol, 6:1) mixture. Mix until the components are completely dissolved.
5) Place the reaction flask on a rotary evaporator and completely evaporate the organic solvent (typical working conditions are: bath at 30° C., rotation speed of about 140 rpm (revolutions per minute) and controlled pressure drops up to 200 mbar (20 kPa), and from this point on, reduce the pressure very slowly (or increase the vacuum very slowly) to the minimum possible over a period of 10 minutes). Is very important that once the solvent evaporates, a homogeneous lipid film remains at the bottom of the flask. If not, the reagents must be redissolved in 7 mL of the chloroform-methanol mixture and evaporated again.
6) Keep the flask with the film at maximum vacuum for at least 15 minutes.
7) Break the vacuum slowly and place the flask for a minimum of 1 hour under nitrogen or argon gas stream, or keep it in a high vacuum desiccator until the next day, to favor the total evaporation of organic solvents Phase 2: Lipid Film Rehydration
8) Heat the aqueous solution with the active principle to be encapsulated (uric acid) above the phase transition temperature (Tm) of the lipids used (65° C. in the present case), maintaining this temperature throughout the process.
9) Heat an extrusion system to the same temperature. In the present case, a 10 mL LIPEX Thermobarrel extruder from Evonik Industries was used, connected to a thermostatic water recirculation bath and a nitrogen gas stream, as the driving gas.
10) Place the reaction flask with the lipid film in water bath until reaching working temperature and then add 7 mL of the aqueous solvent prepared in step 8 and stir until the film is completely dissolved (the process can be facilitated adding a few units of glass beads of about 3 mm in diameter). Maintain stirring for about 10 min, with the flask always in the bath to avoid the temperature to drop below Tm.

Phase 3: Liposome Extrusion
11) With the extruder balanced at a temperature above Tm (65° C. in the present case), wash it 3 times with a generous amount of aqueous solvent (prepared in step 8 explained above).
12) Mount a 0.4-micron pore size polycarbonate membrane on the extruder (Millipore) and wet it with solvent (lithium chloride solution).
13) Fill the extruder with the aqueous lipid mixture and allow the temperature to equilibrate (approximately 10 min).
14) Use a nitrogen or argon gas stream to force extrusion of the mixture through the membrane. Sample must be collected in a hot container, at a temperature above Tm (working temperature must never be lost).
15) Repeat the extrusion process on the 0.4-micron membrane one more time.
16) Repeat the process (4 times) using now a membrane, in this case 0.2 microns and, finally, repeat the extrusion process (8 times) using a 0.1-micron pore size membrane (in total extrusion process involves 2×0.4 microns+4×0.2 microns and 8×0.1 microns), to obtain nominal size liposomes (hydrodynamic diameter) around 100 nanometers (0.1 microns).

Phase 4: Liposome Filtration

The last step in liposome preparation consists of filtering the extruded solution through molecular mass cut filter systems (Amicon systems, for example) or subjecting them to dialysis processes. In this way, individual components that have not been integrated into liposomes are eliminated and their final concentration is adjusted (adjustment of the final volume of solution) and it is possible, if desired, to change aqueous solvent used for preparation of liposomes by another solvent of a hydrophilic nature (for example, by Serum or saline solution)

17) Fill a centrifugal filter unit (Amicon tube (or similar)) with 30 kDa cut-off membrane with solvent and filter it in a centrifuge (2 hours at 6000 g and at room temperature). Perform this filtering 3 times.

18) Pass the extruded liposome solution through the previously washed centrifugal filter unit (step 17) and centrifuge (2 hours at 6000 g).

19) Adjust the final volume of the liposome solution to the desired value (for example, 10 mL) and adjust the pH to the desired value (typically 7.2-7.4) with a few drops of HCl (1N) or NaOH (1N).

The liposomes thus prepared, according to the state of the art, can normally be stored at room temperature (or at 4° C. if preferred or if encapsulating agent so requires) for a prolonged period of time from days to months, depending on the composition thereof. In the specific case of uric acid liposomes, this state-of-the-art methodology was not adequate for two main reasons:

1) Low solubility of uric acid in organic solvents useful for the preparation of lipid films in the formation of liposomes (which prevented its incorporation into liposomes as part of the film, i.e., in step 4 described above) and the great instability which presents this compound in aqueous solutions (tendency to precipitate rapidly) under normal working conditions, made its incorporation into liposomes in stages 8-10 inefficient.

2) The fact that, after preparation, the liposomes encapsulating uric acid were not very stable in solution: In a period ranging from minutes to a few days, the precipitation of encapsulated uric acid was observed.

b) Method of the Present Invention

The process objective of the present invention as indicated above was to solve the problems observed with the state of the art process and to be able to obtain uric acid liposomes with two main features:

1) That they were stable in solution at 4° C. or higher (room temperature) temperatures for a period of at least 21 days.

2) That said liposomes present a minimum amount of uric acid of 1.6 mg/ml (or 9.5 mM) in solution.

With respect to what was indicated above in relation to the state of the art liposome manufacturing process, the manufacturing process of the liposomes that encapsulate uric acid of the present invention presented the following modifications:

1) For the lipid film formation, the steps explained above in the state of the art method were followed, but with the following composition for the lipid bilayer or liposome membrane:DSPC:DC-Cholesterol: 18:0 PEG2000-PE (0.617:0.333:0.050).

TABLE 2

| Molecular weight, molar fraction and total amount of each of the liposome components to obtain 100 μmol of liposomes in the method of the present invention. | | | |
|---|---|---|---|
| components | Molecular weight (g/mol) | Amount (mg) | Molar fraction |
| DSPC (18:0 PC) | 790.1 | 48.72 | 0.617 |
| 18:0 PEG2000 PE | 2805.5 | 14.04 | 0.050 |
| DC-Cholesterol | 537.26 | 17.89 | 0.333 |

2) Preparation of the uric acid solution in aqueous medium and Phase 2:

To rehydrate the lipid film (Stage 2, steps 8-10 of the state of the art process) it was necessary to use an uric acid aqueous solution. This stage was essential in the preparation of uric acid liposomes and was key in obtaining liposome compositions of adequate concentration and stable over time. The process for preparing these solutions is described below and was:

a) Prepare a 40 mM Lithium Chloride Solution (1.696 g/l).

It was essential to use water that did not contain even traces of calcium ions (and preferably avoid the presence of sodium and carbonate ions). Distilled water, MilliQ or the like, as well as saline solutions, phosphate buffered saline or others, which are commonly used in laboratories for liposome synthesis were not suitable. With traces of calcium ions, uric acid solutions were unstable and tended to precipitate over time. Therefore, HPLC (High Performance Liquid Chromatography) grade water (Water, HPLC for Gradient Analysis, Fisher Chemical Ref 10449380) was used.

Since uric acid is divalent, the concentration of lithium chloride (or lithium and/or potassium salt) was at least twice that of uric acid since there must be at least twice as much lithium as uric acid (e.g., for an uric acid solution 20 mM, at least lithium chloride 40 mM was used). If a lower concentration is used, uric acid will end up precipitating over time, faster and in greater quantity the lower the concentration of lithium chloride.

Once the lithium chloride solution was prepared, was essential to adjust the pH to a value between 10 and 11 using, for example, KOH 1M on demand. A pH meter electrode was introduced into the LiCl solution, and the pH was adjusted until it was in the desired range. The used KOH solution (or any other solution used in this step) did not contain calcium ions traces.

Next, uric acid was added:

b) Prepare a 20 mM Uric Acid Solution (3.362 g/l).

At this point, uric acid was added little by little (adequate mass so that the final concentration was over 20 mM). It was essential to continuously monitor the solution pH as the solid uric acid was added to the LiCl, and that the pH never fell below 10 or rise above 11. In any case, the pH had to be corrected by adding a few drops of KOH 1M or HCl 1M so that the pH remained in 10-11 range.

The HCl and KOH 1M solutions did not contain traces of calcium ions.

At the end of the dissolution of all the uric acid in the lithium chloride solution, a clear solution was obtained, with no turbidity; the pH was lowered very slowly to 7.2-7.4 using a few drops of HCl 1M (solution without calcium traces).

The final result of this process was a uric acid solution 20 mM in LiCl 40 mM with pH 7.2-7.4, totally transparent, and which was stable at room T (and at 4° C.) for days. With this solution, the lipid film formed in phase 1 was rehydrated, following steps 8-10 as previously described (Working temperature T=65° C.) (i.e., as in the method for manufacturing or preparation liposome of the state of the art).

In the process of the present invention, a lithium chloride solution was required (calcium ions free, for example using HPLC water, as already described) with a 0.65 g/l (0.65% weight/volume (w/v)—15 mM) concentration at pH 7.2-7.4 which was used as an aqueous solvent (even for cleaning material) in all steps of the liposome preparation process of the present invention.

C) Liposomes Extrusion and Filtration (Phases 3 and 4)

Extrusion followed the same steps as those indicated in the state of the art method, but in any case, the 0.65% (w/v) LiCl solution (15 mM) was used as solvent.

Filtration followed the same steps as those indicated in state of the art method using as solvent the 0.65% (w/v) LiCl solution (15 mM) that was adjusted to 10 mL and to pH 7.2-7.3 with KOH 1M, or HCl 1M, as required.

Following all these modified steps, a clear solution (with no turbidity) of uric acid liposomes (which encapsulate said uric acid) was obtained, which had about a 11 mM concentration of said uric acid (the exact amount will depend on the performance of the synthesis process).

Results Obtained:

26 batches of uric acid liposomes were prepared.

1—liposomes preparation according to the conventional method of the state of the art explained above in this example, including the use of phosphate buffer saline as a vehicle Batches: 3 Batches with Problems: 3 Failed Batches: 100%

2—liposomes preparation according to the conventional method of the state of the art explained above in this example, but with pH control by dissolving uric acid and the use of Saline Serum as a vehicle Batches: 10 Batches with Problems: 4 Failed Batches: 40%

3—Preparation of liposomes according to the conventional method of the state of the art explained above in this example, with pH control when dissolving uric acid and of the final solution of liposomes, use of HPLC water in synthesis and use of LiCl 0.65% w/v as a vehicle (material washes made with MiliQ water)

Batches: 7 Batches with Problems: 1 Failed Batches: 14%

4—Process of the present invention (the entire process done with HPLC water, including material washing)

Batches: 6 Batches with Problems: 0 Failed Batches: 0%

Observed problems in the cases of batches 1 to 3 were basically formation of uric acid crystals in suspension and precipitation, at different times, after preparation. Surprisingly, with the process of the present invention, all these problems were solved, and all the manufactured batches were successful.

Example 2. Characterization of the Liposomes Obtained by the Method of the Present Invention Following the method of the present invention described in Example 1, 22 batches of uric acid liposomes (AU liposomes) and 22 batches of liposomes of identical composition, but with no uric acid inside (control liposomes) were prepared. Each of the preparations was characterized, as indicated below.

1) Size and z-Potential of Liposomes.

Liposomes size (in the form of hydrodynamic diameter) and Z potential determination was done by means of DLS, for which a Malvern z-sizer equipment was used, operated according to the manufacturer's instructions, at a temperature of 25° C. Briefly, for this, a 100-microliter sample was extracted from the final liposome solution, bringing it to 1 mL (dilution 1 to 10) in HPLC grade water that was introduced into a cuvette. The equipment was turned on and the laser was allowed to stabilize for at least 30 minutes. The sample was then thermostated in the cuvette inside the equipment for at least 3 minutes, to proceed later with the measurement. In no case the sample concentration was greater than 1 mg/mL.

The size (in the form of hydrodynamic diameter), polydispersity and potential Z obtained was indicated in Table 3 included below:

TABLE 3

| Liposomes that encapsulate uric acid obtained according to the method of the present invention and control liposomes size and Z potential. | | | |
| --- | --- | --- | --- |
| Sample | Hydrodynamic diameter (in nm) | Polydispersity | Z Potential (mV) |
| AU liposomes | 113.3 ± 13.7 | 0.008 ± 0.003 | 10.42 ± 2.1 |
| Control liposomes | 104.1 ± 9.4 | 0.010 ± 0.008 | 10.43 ± 1.0 |

2) Production Performance

Is normal that in the multiple stages involved in the synthesis, extrusion and filtering of liposomes, a certain amount of material is lost. To determine the performance of the process of the present invention, the amount of lipids in the final liposome solutions was determined, using the well-known Rouser colorimetric method (Rouser G, Fkeischer S, Yamamoto A. Two dimensional then layer chromatographic separation of polar lipids and determination of phospholipids by phosphorus analysis of spots. Lipids. 1970 May; 5(5):494-6. doi: 10.1007/BF02531316. PMID: 5483450).

TABLE 4

| Yield results in production obtained in Example 2. | | | |
| --- | --- | --- | --- |
| Sample | Heavy lipids (μmol) | Final lipids (μmol) | Yield (%) |
| AU liposomes | 66.7 ± 0.02 | 44.4 ± 2.5 | 66.6 ± 3.7 |
| Control liposomes | 66.7 ± 0.02 | 44.9 ± 0.9 | 67.3 ± 1.4 |

3) Encapsulation Efficiency

In each uric acid liposomes preparation, the exact amount of therapeutic agent encapsulated in the liposomes was calculated using a colorimetric technique based on the uricase digestion method described by Hamzah H H et al. (Hamzah H H, Zain Z M, Musa N L W, Lin Y C, Trimbee E (2013) Spectrophotometric Determination of Uric Acid in Urine Based-Enzymatic Method Uricase with 4-Aminodiphenylamine Diazonium Sulfate (Variamine Blue RT Salt). J Anal Bioanal Tech S7: 011. doi:10.4172/2155-9872.S7-011). In summary, 25 μL of non-encapsulated uric acid solution were taken (after encapsulation, the non-encapsulated uric acid sample is obtained in the filtration phase by centrifugation), 25 μL of Variamin 0.1 mM and 50 μL of uricase (50 μg/ml), bringing the final volume to 1 ml. The mixture was kept at 37° C. for 30 minutes and the amount of uric acid in solution was determined by measuring the absorbance at 261 nm, determining the concentration by means of a calibration line obtained from standard uric acid solutions measured in the same way.

To calculate encapsulation efficiency, the exact uric acid amount added in each liposome preparation was recorded in phase 2 of the liposome preparation process of the present invention (hydration of the lipid film) and the non-encapsulated uric acid amount was determined by colorimetry, from the obtained filtrate in phase 4 of the liposome preparation process of the present invention (filtrate in an Amicon tube with a cut-off point of 30 kDa). Obtained results are summarized in Table 5 included below:

TABLE 5

Yield results in encapsulation obtained in Example 2 for the liposome preparation process of the present invention.

| Sample | Initial uric acid (μmol) | Encapsulated uric acid (μmol) | Encapsulation Efficiency (%) |
|---|---|---|---|
| AU liposomes | 140.58 ± 0.26 | 112.01 ± 8.68 | 79.7 ± 6.2 |

4) Liposomes Stability

Finally, a study was carried out in which stability of the liposomes in solution at room temperature was observed for a period of 21 days. In this period, no turbidity or precipitate formation was observed. On the other hand, the liposomes were filtered every 3-7 days and the uric acid amount that remained encapsulated and which part had been released in solution were determined, using the colorimetric method described in the previous section. Obtained results showed that 7 days after the liposomes synthesis or elaboration, more than 90% of uric acid remained encapsulated while less than 10% had been released, the liposomes remaining, therefore, stable in solution. At 15 and 21 days from the liposomes synthesis or elaboration, the initial uric acid that remained encapsulated amounts were greater than 80%, demonstrating the great stability of the liposomes (see FIG. 1). It is important to note that despite the fact that at long storage times a small portion of uric acid is released in solution (released from liposomes), the solutions retained their transparency and uric acid crystallization was not observed.

Example 3. Analysis of Different Compositions of the Lipid Bilayer in Liposomes that Encapsulate Uric Acid Four different lipid compositions used in the process of the present invention were analyzed for the preparation of liposomes that encapsulate uric acid:

1—DOPE:cholesterol:18:0 PEG2000-PE Molar fractions (0.583:0.333:0.083)
2—DSPC:Cholesterol:18:0 PEG2000-PE Molar fractions (0.583:0.3333:0.083)
3—DOTAP:DSPC:Cholesterol:18:0 PEG2000-PE Molar fractions (0.3:0.283:0.33:0.083)
4—DSPC:DC-Cholesterol:18:0 PEG2000-PE Molar fractions (0.617:0.333:0.050)
DOPE: 18:1 (Δ9-Cis) PC (DOPC) 1,2-dioleol-sn-glycero-3-phosphocholine
DOTAP: N-[1-(2,3-Dioleoyloxy) propyl]-N, N, N-trimethylammonium The lipid bilayer compositions 1 to 3 showed non-optimal results of encapsulation and uric acid release and lower than those of 4, which did show optimal results of encapsulation and uric acid release. Specifically, it was observed that the kinetics of uric acid release from the liposomes to dissolution were faster in compositions 1 to 3, compared to 4, in such a way that 7 days after preparation less than 65% of the UA remained. encapsulated in the liposomes of formulations 1 to 3 (compared to 90% of formulation 4) and after 15 days less than 45% of the UA remained encapsulated in the liposomes of formulations 1 to 3 (compared to 80% of formulation 4).

Example 4. Efficacy Analysis of Uric Acid Liposomes of the Present Invention in a Mouse Model of Cerebral Ischemia/Reperfusion In this example, the liposomes of the present invention efficacy was analyzed in a mouse model of brain ischemia/reperfusion. The experimental details were as follows:
    Species: Mouse C57BL/6 from the supplier "Laboratorios Janvier"; sex: males; age: 10 to 14 weeks.
    Dose: 16 mg uric acid/kg mouse weight.
    Ischemia/reperfusion: 30 min middle cerebral artery occlusion (MCAO) (monitored with laser Doppler) followed by 24 h of reperfusion.
    Treatment: a) Intravenous infusion (20 minutes duration) of the different treatments. Treatment began 30 min after reperfusion. Treatments were administered blind.
    Neurological test: At 24 h the neuroscore was performed.
    Euthanasia: After neurological test, the animals were sacrificed. Blood samples were taken, and the brain was extracted which was cut out for staining with TTC (tetrazolium chloride) to measure the cerebral infarct volume.
    Inclusion/exclusion criteria: All mice that had a drop in blood flow greater than 65% and a reperfusion greater than 70% received the treatment. Of these, animals were not included if the injection was not correct. Of the correctly administered animals, mice that did not develop an infarct or with a very small infarct (<10%), and mice that had an infarct outside the territory of the middle cerebral artery were excluded. Animals that died were counted but were not included in the study due to the lack of volume/neuroscore data at end point.
    See summary of the experimental protocol included in FIG. 2.

The treatment was randomized, and the administration of the drugs was performed blind. The treatment groups were:
    a) Liposomes that encapsulate uric acid diluted in saline solution (Lipo-UA) (Liposomes according to the present invention).
    b) Empty liposomes diluted in saline solution (Lipo) (i.e., liposomes prepared according to the method of the present invention but with no uric acid).
    c) Uric acid solution (dissolved in mannitol and lithium) (UA).
    d) Corresponding vehicle (V): is the same solution as that used in group c) but with no uric acid (that is, a mannitol and lithium solution with no uric acid).
Results:
    Table 6 includes a summary of the animals included in each of the experimental groups:

TABLE 6

Summary of the mice included in each of the experimental groups of Example 4. The numbers indicated in the table refer in all cases to the number of mice.

| | Lipo-UA | Lipo | UA | V |
|---|---|---|---|---|
| Total | 18 | 20 | 16 | 18 |
| Excluded | 1 | 5 | 4 | 3 |
| Included | 16 | 15 | 12 | 13 |

TABLE 6-continued

Summary of the mice included in each of the experimental groups of Example 4. The numbers indicated in the table refer in all cases to the number of mice.

|  | Lipo-UA | Lipo | UA | V |
|---|---|---|---|---|
| Mortality | 1 | 0 | 0 | 2 |
| Mortality % | 5.6% | 0% | 0% | 11% |

Analysis of the results was done in a blinded mode.

The obtained results for the cerebral infarction volume and neuroscore in the different experimental groups are summarized in FIGS. 3 and 4.

Administration of Lipo-UA produced a significant decrease (31.79%) in the volume of the cerebral infarct compared to the control group (Lipo) (see FIG. 3).

UA administration produced an also significant decrease (28.61%) in the cerebral infarct volume compared to the control group (vehicle; V) (see FIG. 3).

Treatment with Lipo-UA and treatment with UA caused a similar reduction in cerebral infarct volume, however, a tendency was observed for the effect to be greater with Lipo-UA (see FIG. 3).

Additionally, and surprisingly, treatment with Lipo-UA produced an improvement in neurological function as deduced from the significant reduction (25.6%) in the neuroscore test score. This effect was not observed in UA treatment (see FIG. 4) Additionally, it was possible to corroborate that the liposomes of the present invention reached the blood capillaries of the brain effectively (see example 5 and FIG. 5).

Finally, the liposome manufacturing method effect on their effectiveness was also studied. For this, the same protocol indicated above was followed but with uric acid liposomes prepared according to the state of the art method and uric acid liposomes prepared according to the method of the present invention. The results obtained were those shown in Tables 7 and 8 included below:

TABLE 7

Results obtained with uric acid liposomes prepared according to the state of the art method.

|  | Lipo | Lipo-UA | Reduction % | p |
|---|---|---|---|---|
| No. of mice | 7 | 7 |  |  |
| Cerebral infarct volume (mm³) | 42.57 | 40.03 | 5.97 | p = 0.6983 |
| Cerebral infarction volume (% with respect to the volume of the corresponding hemisphere (corrected for edema)) | 26.24 | 23.99 | 8.57 | p = 0.5590 |
| Neuroscore | 11.29 | 9.71 | 13.96 | p = 0.4202 |

TABLE 8

Obtained results with uric acid liposomes prepared according to the method of the present invention.

|  | Lipo | Lipo-UA | Reduction % | p |
|---|---|---|---|---|
| No. of mice | 10 | 9 |  |  |
| Cerebral infarct volume (mm³) | 45.53 | 31.86 | 30.02 | p = 0.0215 |
| Cerebral infarction volume | 27.26 | 19.83 | 27.26 | p = 0.0222 |

TABLE 8-continued

Obtained results with uric acid liposomes prepared according to the method of the present invention.

|  | Lipo | Lipo-UA | Reduction % | p |
|---|---|---|---|---|
| (% with respect to the volume of the corresponding hemisphere (corrected for edema)) |  |  |  |  |
| Neuroscore | 9.60 | 7.89 | 17.82 | p = 0.1216 |

As derived from Tables 7 and 8, the method of the present invention makes it possible to obtain liposomes that encapsulate uric acid that show a greater therapeutic effect (in the form of a smaller volume of cerebral infarction and a better neuroscore) compared to uric acid liposomes obtained with the process of the state of the art.

Example 5. Study of the Localization of Liposomes of the Present Invention in the Mouse Brain In this case, the ischemic mice (obtained as indicated in Example 4) were administered liposomes of the present invention (with uric acid) or control liposomes (with saline solution), all of them with a green fluorescent protein (Dioc18), according to the liposome administration method set forth above. Two hours after reperfusion, euthanasia was carried out, the brain was fixed with 4% paraformaldehyde, and the tissue was processed for immunofluorescence and confocal microscopy. For this, coronal sections of the brain were made with vibratome (50 μm thick) that were cryoprotected in glycerol and stored at −20° C. Blood vessels were stained with the anti-Glut1 antibody followed by a secondary antibody AlexaFluor-556 (red). Nuclei are visualized with DAPI staining (blue). A confocal microscopy study (DragonFly) was carried out, making 1 μm planes to carry out a co-localization study with the ImageJ software (Colocalization threshold). FIG. 5 shows a representative image that illustrates the presence of the green fluorescent protein Dioc18 in the capillary wall (red) after the liposomes that encapsulate uric acid and Dioc18 administration.

Therefore, Examples 1 to 5 demonstrate that the inventors of the present invention have been able to effectively obtain liposomes that encapsulate uric acid, that said liposomes are stable over time and are superior (superior therapeutic effect) for the treatment of stroke.

Additionally, the results collected in examples 1 to 5 demonstrate the surprising results obtained with the process of the present invention for the preparation of liposomes that encapsulate uric acid, both in terms of performance and stability, as well as a surprising superior therapeutic effect.

The invention claimed is:

1. Liposome that encapsulates uric acid, uric acid salts, or combinations thereof, wherein said liposome has a lipid bilayer comprising double-chain phospholipids and positively charged cholesterol, wherein said liposome is unilamellar.

2. The liposome according to claim 1, wherein the encapsulated amount of uric acid is between $6*10^{-20}$ and $6*10^{-18}$ moles per liposome.

3. The liposome according to claim 1, wherein said liposome has a hydrodynamic diameter measured by Dynamic Light Scattering (DLS) in water at a temperature of 25° C. of between 80 and 140 nm.

4. The liposome according to claim 1, wherein said liposome has a positively charge surface and a Z potential measured by Dynamic Light Scattering (DLS) at a temperature of 25° C. greater than 0 and lower than 15 mV.

5. The liposome according to claim 1, wherein between 2.5% and 10% molar of the double-chain phospholipids are phospholipids with one or more polyethylene glycol chains attached to a polar head that hinder the opsonization of blood liposomes attached to a polar head of said phospholipids; and between 90 and 97.5% molar of the double chain phospholipids are phospholipids with no polyethylene glycol attached to a polar head of said phospholipids.

6. The liposome of claim 5, wherein:
said double chain phospholipids with one or more polyethylene glycol chains attached to a polar head are selected from 16:0 PEG2000 PE (or 1,2 dipalmitoyl-sn-glycero-3-phosphoethanolamine-N-[methoxy (polyethylene glycol)-2000]), 18:0 PEG2000 PE (or 1,2-distearoyl-sn-glycero-3-phosphoethanolamine-N-[methoxy (polyethylene glycol)-2000]), 18:0 PEG5000 PE (or 1,2-distearoyl-sn-glycero-3-phosphoethanolamine-N-[methoxy (polyethylene glycol)-5000]) or combinations thereof; and
said double chain phospholipids without polyethylene glycol attached to a polar head are selected from DSPC (18:0 PC or 1,2-distearoyl-sn-glycero-3-phosphocholine), DPPC (16:0 PC or 1, 2-dipalmitoyl-sn-glycero-3-phosphocholine)), 17:0 PC (or 1,2-diheptadecanoyl-sn-glycero-3-phosphocholine) or combinations thereof.

7. The liposome according to claim 1, wherein said positively charged cholesterol is dimethylaminoethane-carbamoyl-cholesterol (DC-cholesterol) hydrochloride.

8. The liposome according to claim 7, comprising a molar fraction ratio between double chain phospholipids and DC-cholesterol between 0.6:0.4 and 0.75:0.25.

9. A method for the manufacture of liposomes that encapsulate uric acid, uric acid salts, or combinations thereof, said method comprising the steps of:

a) preparing a solution comprising lithium and/or potassium ions in water;

b) adjusting said solution to a pH value between 10 and 11;

c) adding uric acid, uric acid salts, or combinations thereof, in which the lithium and/or potassium ions are present in an molar amount that is at least twice than of uric acid, keeping the pH in the range of 10-11 to obtain a complete dissolution;

d) lowering the pH to a value between 7.2 and 7.4 to obtain a uric acid solution;

e) forming a lipid film;

f) rehydrating the lipid film formed in step e) with the uric acid solution of step d) to obtain liposomes;

g) extruding the obtained liposomes in step f) using the lithium and/or potassium ions solution of step a) as solvent; and h) filtering the obtained liposomes in step g) using the lithium and/or potassium ions solution of step a) as solvent, wherein steps e) to h) are carried out free of calcium ions.

10. A pharmaceutical composition comprising a liposome according to claim 1 and at least one pharmaceutically acceptable excipient.

11. A medicine comprising the pharmaceutical composition according to claim 10.

12. A method for improving and/or treating cerebrovascular disease comprising administering the pharmaceutical composition according to claim 10 to a patient in need thereof.

13. A medicine comprising the liposome according to claim 1.

14. A method for improving and/or treating cerebrovascular disease comprising administering the liposome according to claim 1 to a patient in need thereof.

* * * * *